US011511050B2

(12) United States Patent
Nakajima et al.

(10) Patent No.: US 11,511,050 B2
(45) Date of Patent: Nov. 29, 2022

(54) NEEDLE ASSEMBLY

(71) Applicant: TERUMO KABUSHIKI KAISHA, Tokyo (JP)

(72) Inventors: Kentaro Nakajima, Yamanashi (JP); Yoichiro Iwase, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 214 days.

(21) Appl. No.: 16/815,510

(22) Filed: Mar. 11, 2020

(65) Prior Publication Data

US 2020/0206435 A1 Jul. 2, 2020

Related U.S. Application Data

(63) Continuation of application No. PCT/JP2019/009105, filed on Mar. 7, 2019.

(30) Foreign Application Priority Data

Mar. 16, 2018 (JP) .............................. JP2018-049361

(51) Int. Cl.
*A61M 5/32* (2006.01)

(52) U.S. Cl.
CPC ........ *A61M 5/3245* (2013.01); *A61M 5/3271* (2013.01); *A61M 5/3293* (2013.01);
(Continued)

(58) Field of Classification Search
CPC .............. A61M 5/3271; A61M 5/3293; A61M 5/3272; A61M 2005/3217; A61M 2005/3247; A61M 2005/3267
See application file for complete search history.

(56) References Cited

U.S. PATENT DOCUMENTS 9,333,306 B2 * 5/2016 Cross .................. A61M 5/3272
2009/0024093 A1 1/2009 Carrel et al.
(Continued)

FOREIGN PATENT DOCUMENTS

JP 2008536598 A 9/2008
JP 2013529988 A 7/2013
(Continued)

OTHER PUBLICATIONS

International Search Report (PCT/ISA/210) and translation and Written Opinion (PCT/ISA/237) dated May 14, 2019, by the Japanese Patent Office as the International Searching Authority for International Application No. PCT/JP2019/009105.
(Continued)

*Primary Examiner* — Laura A Bouchelle
(74) *Attorney, Agent, or Firm* — Buchanan Ingersoll & Rooney PC

(57) ABSTRACT

A needle assembly is disclosed, which includes a needle protection member and a rotor. The rotor has a rotor body and a restriction portion. When the needle protection member in the initial state is displaced from the protection position to a use position and returns to a protection position, the restriction portion is displaced from the initial position to the lock position by the rotation of the rotor body with respect to the needle protection member. A needle hub has a displacement prevention portion that prevents the needle protection member from being displaced from the protection position to the use position again by contacting the restriction portion at the lock position.

20 Claims, 15 Drawing Sheets

(52) U.S. Cl.
CPC ............... *A61M 2005/3217* (2013.01); *A61M 2005/3235* (2013.01)

(56) References Cited

U.S. PATENT DOCUMENTS

| | | | |
|---|---|---|---|
| 2011/0160675 A1* | 6/2011 | Ruan | A61M 5/3272 604/198 |
| 2013/0261563 A1 | 10/2013 | Zachek et al. | |
| 2013/0324923 A1 | 12/2013 | Roberts et al. | |
| 2015/0057637 A1 | 2/2015 | Herr | |
| 2015/0157808 A1 | 6/2015 | Srinivasan et al. | |
| 2018/0015234 A1 | 1/2018 | Iwase | |
| 2018/0214639 A1 | 8/2018 | Takemoto | |

FOREIGN PATENT DOCUMENTS

| | | | |
|---|---|---|---|
| WO | 2015022787 A1 | 2/2015 | |
| WO | 2016158140 A1 | 10/2016 | |

OTHER PUBLICATIONS

The extended European Search Report dated Aug. 24, 2020, by the European Patent Office in corresponding European Patent Application No. 19766713.2-1122. (9 pages).

* cited by examiner

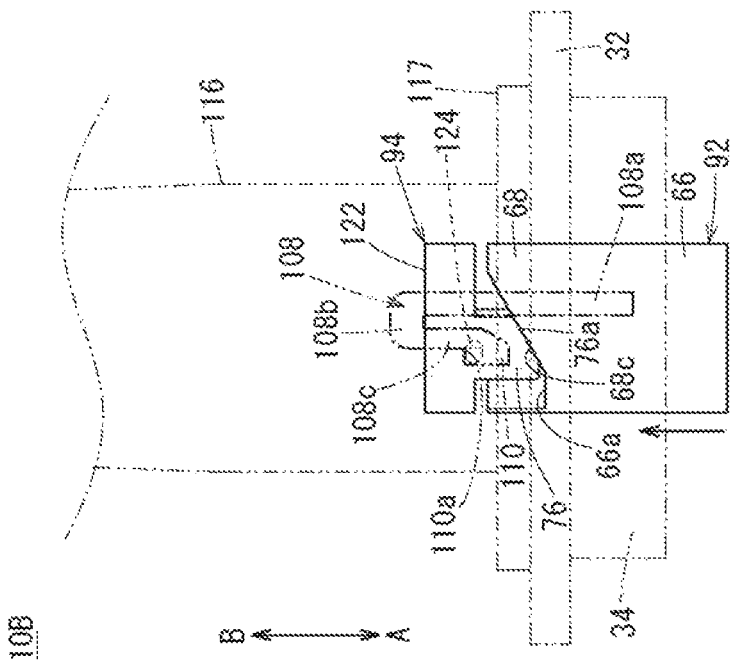
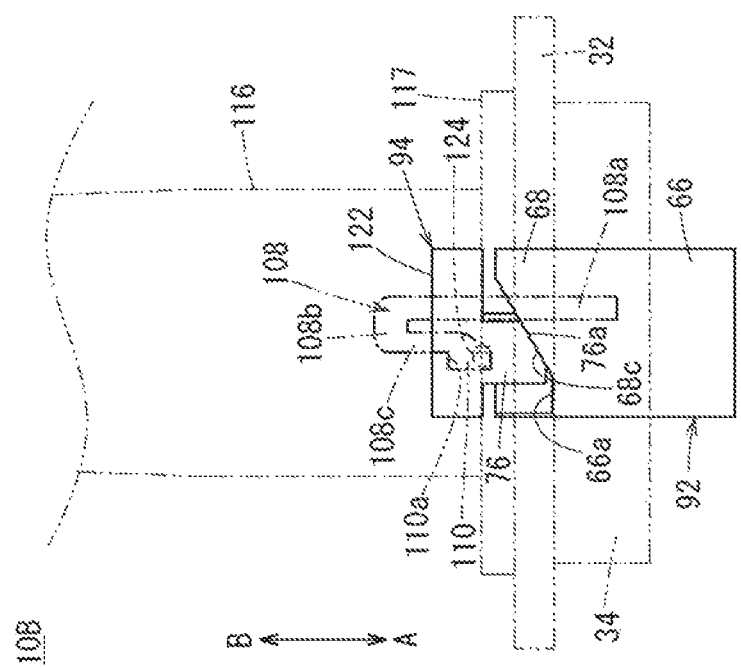

NEEDLE ASSEMBLY

CROSS-REFERENCES TO RELATED APPLICATIONS

This application is a continuation of International Application No. PCT/JP2019/009105 filed on Mar. 7, 2019, which claims priority to Japanese Application No. 2018-049361 filed on Mar. 16, 2018, the entire content of both of which is incorporated herein by reference.

FIELD OF THE DISCLOSURE

The present disclosure generally relates to a needle assembly for injecting a drug intradermally.

BACKGROUND DISCUSSION

A needle assembly for injecting a vaccine (drug), for treating, for example, influenza (flu) intradermally (in the dermis) has been known. This needle assembly includes a needle protection member (protector) that is displaceable along the axial direction of the tubular needle between a protection position for covering the needle tip of the tubular needle and a position in which the needle tip is exposed (i.e., use position).

The needle protection member is displaced from the protection position to the use position while its distal end face is pressed against the skin of the drug recipient and rotated in the circumferential direction of the tubular needle, so that a safety function is activated which prevents the displacement from the protection position to the use position again (see, for example, International Patent Application Publication No. 2016/158140).

In the conventional needle assembly described above, when the needle protection member is displaced from the protection position to the use position, the needle protection member rotates in the circumferential direction of the tubular needle while being in contact with the skin. For this reason, the needle protection member may rotate due to skin resistance, and may not be displaced to the correct use position, so that the safety function may not be activated. In addition, the skin may be pulled in the rotation direction by the needle protection member, and may cause discomfort to the drug recipient.

SUMMARY

A needle assembly is disclosed, which is capable of activating the safety function without fail, and suppressing discomfort given to a drug recipient.

In accordance with an aspect, a needle assembly for injecting a drug intradermally is disclosed, the needle assembly comprising: a tubular needle that includes a needle tip; a needle hub supporting the tubular needle; a displaceable needle protection member provided on the needle hub along an axial direction of the tubular needle; a rotor provided at a proximal end of the needle protection member, the rotor includes a rotor body and a restriction portion, the restriction portion being provided on the rotor body, and wherein the restriction portion is displaced from an initial position to a lock position by the rotor body rotating with respect to the needle protection member; and wherein the needle hub includes a displacement prevention portion configured to prevent the needle protection member from being re-displaced by contacting the restriction portion at the lock position.

In accordance with a further aspect, a needle assembly for injecting a drug intradermally is disclosed, the needle assembly comprising: a tubular needle that includes a needle tip; a needle hub supporting the tubular needle; a needle protection member displaceably provided on the needle hub along an axial direction of the tubular needle; a rotor provided at a proximal end of the needle protection member; an urging member provided on the needle hub to urge the rotor and the needle protection member toward a distal direction of the tubular needle; the needle protection member is located at a use position at which the needle tip is exposed when displaced in a proximal direction of the tubular needle from a protection position at which the needle tip is covered; the rotor includes a rotor body and a restriction portion, the restriction portion being provided on the rotor body, and wherein the restriction portion is displaced from an initial position to a lock position by the rotor body rotating with respect to the needle protection member when the needle protection member in an initial state is displaced from the protection position to the use position and returns to the protection position; and wherein the needle hub is provided with a displacement prevention portion configured to prevent the needle protection member from being re-displaced from the protection position to the use position by contacting the restriction portion at the lock position.

In accordance with another aspect, a needle assembly according to the present disclosure is a needle assembly for injecting a drug intradermally, which includes a tubular needle having a needle tip, a needle hub that holds the tubular needle, a needle protection member displaceably provided on the needle hub along an axial direction of the tubular needle, a rotor provided at a proximal end of the needle protection member, and an urging member provided on the needle hub to urge the rotor and the needle protection member toward a distal direction of the tubular needle, wherein the needle protection member is located at a use position at which the needle tip is exposed when displaced in a proximal direction of the tubular needle from a protection position at which the needle tip is covered, wherein the rotor includes a rotor body, and a restriction portion provided on the rotor body, wherein the restriction portion is displaced from an initial position to a lock position by the rotor body rotating with respect to the needle protection member when the needle protection member in an initial state is displaced from the protection position to the use position and returns to the protection position, and wherein the needle hub is provided with a displacement prevention portion that prevents the needle protection member from being re-displaced from the protection position to the use position by contacting the restriction portion at the lock position.

According to such a configuration, when the needle protection member in the initial state is displaced from the protection position to the use position and returns to the protection position, the rotation of the rotor body causes the restriction portion to be displaced from the initial position to the lock position. As a result, the safety function can be reliably activated. Furthermore, since the needle protection member is not rotated in the circumferential direction of the tubular needle, the discomfort given to the drug recipient due to the skin being pulled in the rotation direction when the needle protection member is displaced from the protection position to the use position can be suppressed.

The above-described needle assembly may include a rotation restriction portion that restricts a rotation of the needle protection member with respect to the needle hub along a circumferential direction of the tubular needle.

According to such a configuration, when the needle protection member is displaced from the protection position to the use position, rotation with respect to the skin can be effectively suppressed.

In the above needle assembly, a proximal end face of the needle protection member may have an inclined surface that is inclined in an axial direction of the tubular needle toward a circumferential direction of the tubular needle, and wherein the rotor may have a protrusion that projects from the rotor body toward the distal direction of the tubular needle and contacts the inclined surface.

According to such a configuration, the rotor can be rotated in the circumferential direction of the tubular needle with respect to the needle protection member with a relatively simple configuration.

In the needle assembly described above, the protrusion may have a contact face that comes into surface contact with the inclined surface.

According to such a configuration, excessive pressure can be prevented from acting on the protrusion from the needle protection member.

In the needle assembly described above, a plurality of the inclined surfaces and a plurality of the protrusions may be provided in the circumferential direction of the tubular needle.

According to such a configuration, it is possible to further prevent an excessive pressure from acting on the protrusion from the needle protection member.

In the needle assembly described above, the restriction portion may project from the protrusion along a radial direction of the tubular needle.

According to such a configuration, the rigidity of the protrusion can be improved by the restriction portion.

In the needle assembly described above, the needle hub may have a recessed guide passage for guiding the restriction portion at the initial position to the lock position.

According to such a configuration, the restriction portion at the initial position can be reliably guided to the lock position.

In the needle assembly described above, the restriction portion may project radially outward of the tubular needle from the protrusion, wherein the needle hub may have an outer tubular portion disposed around an outer periphery of the rotor, wherein the outer tubular portion may have the guide passage, and a recessed lock portion that is located in a distal direction of the tubular needle relative to the guide passage and composes the displacement prevention portion, and wherein when the needle protection member returns from the use position to the protection position by an urging force of the urging member, the restriction portion in the guide passage may get over the displacement prevention portion in the distal direction of the tubular needle to be inserted into the lock portion.

According to such a configuration, the needle hub and the rotor can be simplified.

In the needle assembly described above, slits which are open in a face of the rotor body may be formed on both sides of the restriction portion of the rotor body, where the face is directed toward the proximal direction of the tubular needle, and wherein the rotor body may be elastically deformed radially inward of the tubular needle when the restriction portion gets over the displacement prevention portion.

According to such a configuration, the restriction portion can easily get over the displacement prevention portion.

In the needle assembly described above, the restriction portion may have a tapered face that is inclined radially inward of the tubular needle toward the distal direction of the tubular needle.

According to such a configuration, when the restriction portion gets over the displacement prevention portion, the portion between the slits of the rotor body can be pressed radially inward of the tubular needle.

In the needle assembly described above, the restriction portion may project radially inward of the tubular needle from the protrusion, and wherein the needle hub may have a needle holding body disposed radially inward of the tubular needle relative to the rotor and having the guide passage formed in the needle holding body.

According to such a configuration, the needle hub and the rotor can be made relatively compact.

According to the present disclosure, when the needle protection member in the initial state is displaced from the protection position to the use position and returns to the protection position, the rotation of the rotor body causes the restriction portion to be displaced from the initial position to the lock position, so that the safety function can be reliably activated. That is, it is possible to prevent the fact that the needle protection member rotates insufficiently due to skin resistance, and cannot be displaced to the correct use position, so that the safety function may not be activated. Furthermore, since the needle protection member is not rotated in the circumferential direction of the tubular needle, the discomfort given to the drug recipient due to the skin being pulled in the rotation direction of the needle protection member when the needle protection member is displaced from the protection position to the use position can be suppressed.

BRIEF DESCRIPTION OF THE DRAWINGS

FIG. 15A is a third operation explanatory view of the needle assembly of FIG. 9.

FIG. 15B is a fourth operation explanatory view of the needle assembly of FIG. 9.

DETAILED DESCRIPTION

Set forth below with reference to the accompanying drawings is a detailed description of embodiments of a needle assembly for injecting a drug intradermally representing examples of the inventive needle assembly for injecting a drug intradermally disclosed here.

First Embodiment

Figure 6:
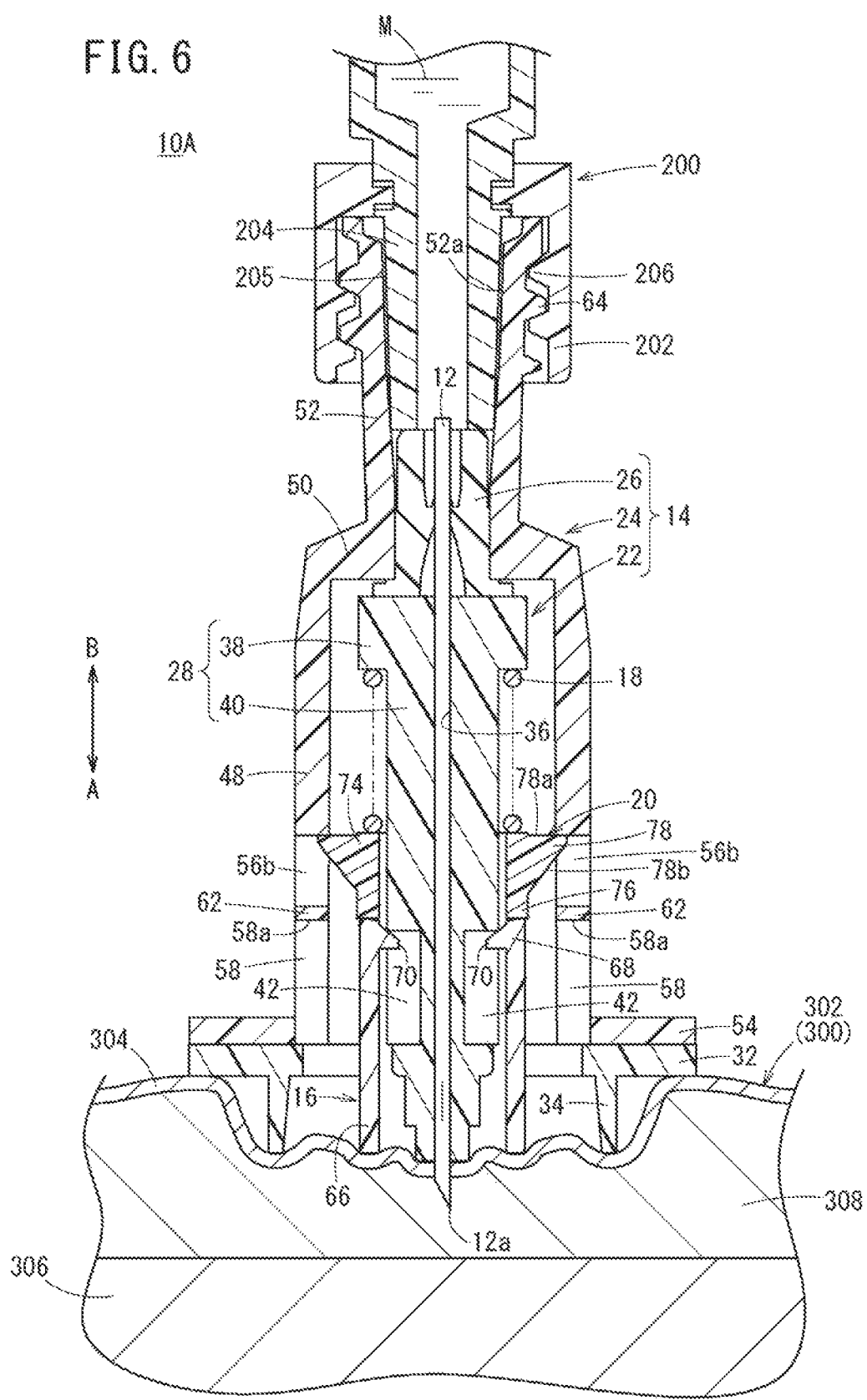
FIG. 6 is an explanatory sectional view showing a state where a drug is injected intradermally by the needle assembly of FIG. 1.
Figure 7:
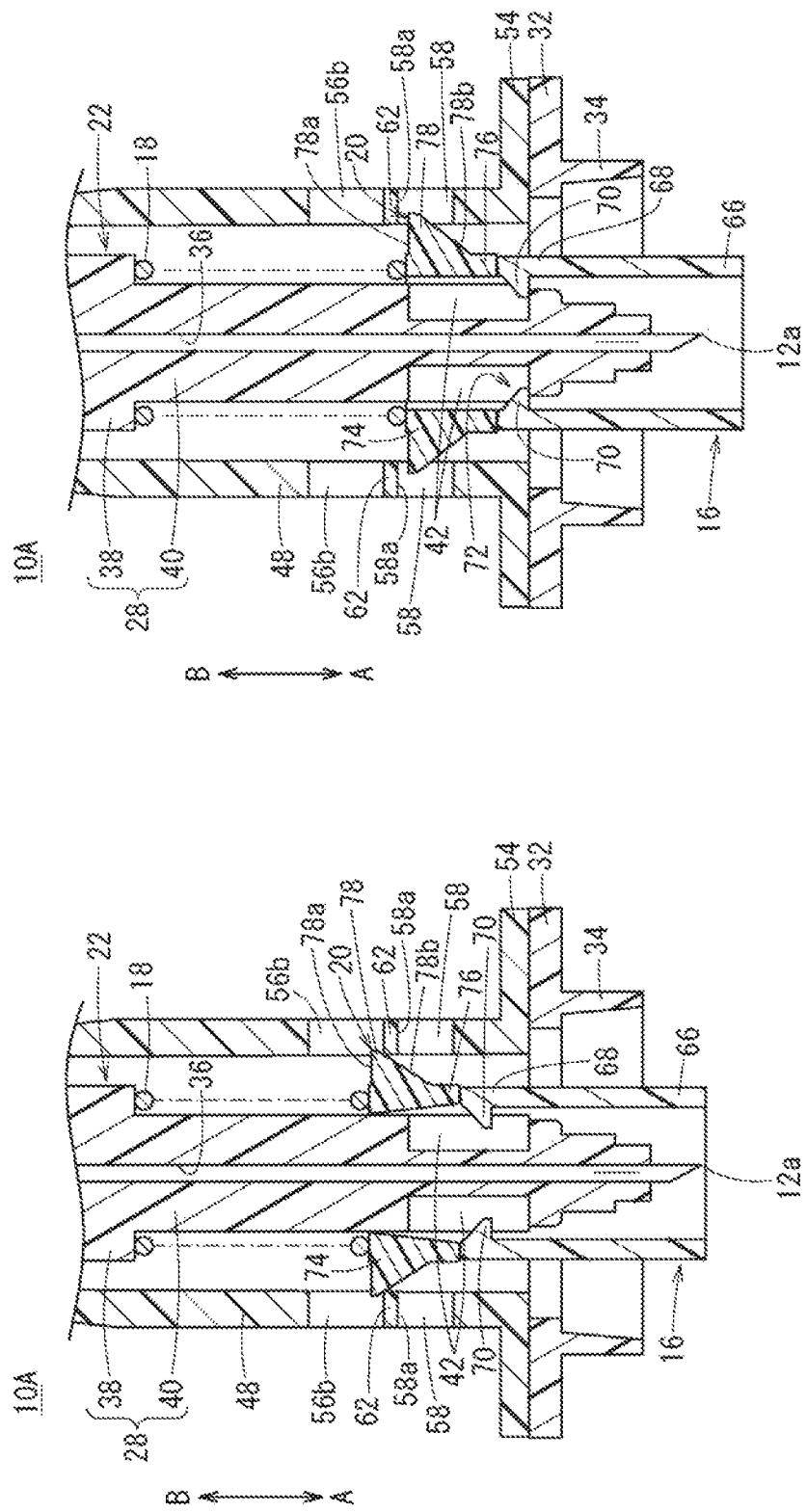
FIG. 7A is a third operation explanatory view of the needle assembly of FIG. 1.
FIG. 7B is a fourth operation explanatory view of the needle assembly of FIG. 1.
Figure 8:
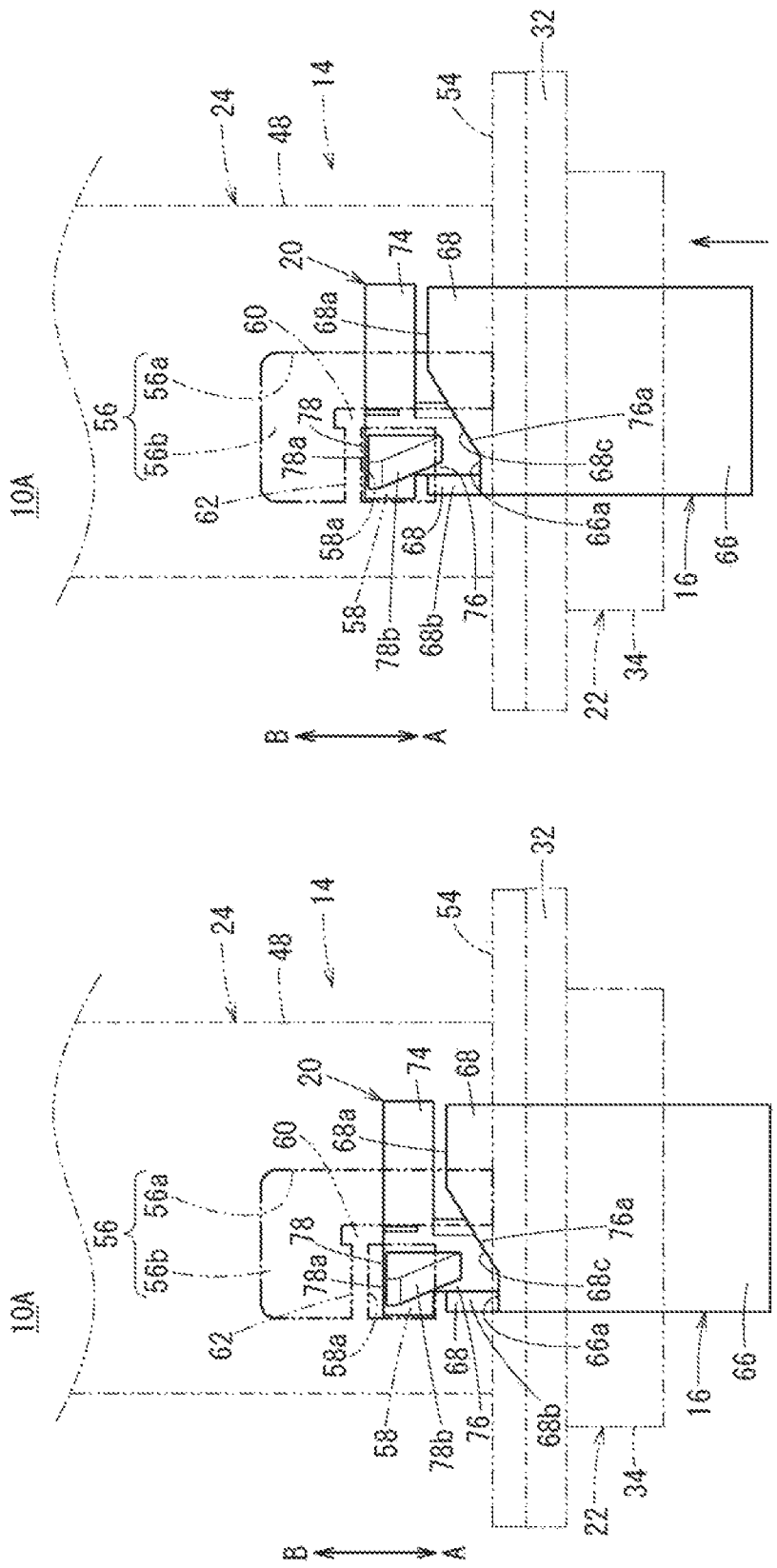
FIG. 8A is a fifth operation explanatory view of the needle assembly of FIG. 1.
FIG. 8B is a sixth operation explanatory view of the needle assembly of FIG. 1.

As shown in FIG. 6, a needle assembly 10A according to the first embodiment of the present disclosure, is a device for injecting a drug M intradermally 308 (in the dermis) between the epidermis 304 and the subcutaneous tissue 306 of the skin 302 of the drug recipient 300 (see FIG. 6).

An example of the drug M includes a vaccine for preventing infectious diseases such as influenza (i.e., flu). However, drug M is not limited to vaccines. For example, drug M may be carbohydrate injection solution such as glucose, electrolyte correction injection solution such as sodium chloride and potassium lactate, vitamins, antibiotic injection solution, contrast agents, steroids, protease inhibitors, fat emulsions, anticancer agents, anesthetics, Heparin calcium, antibody drugs and the like.

Figure 2:
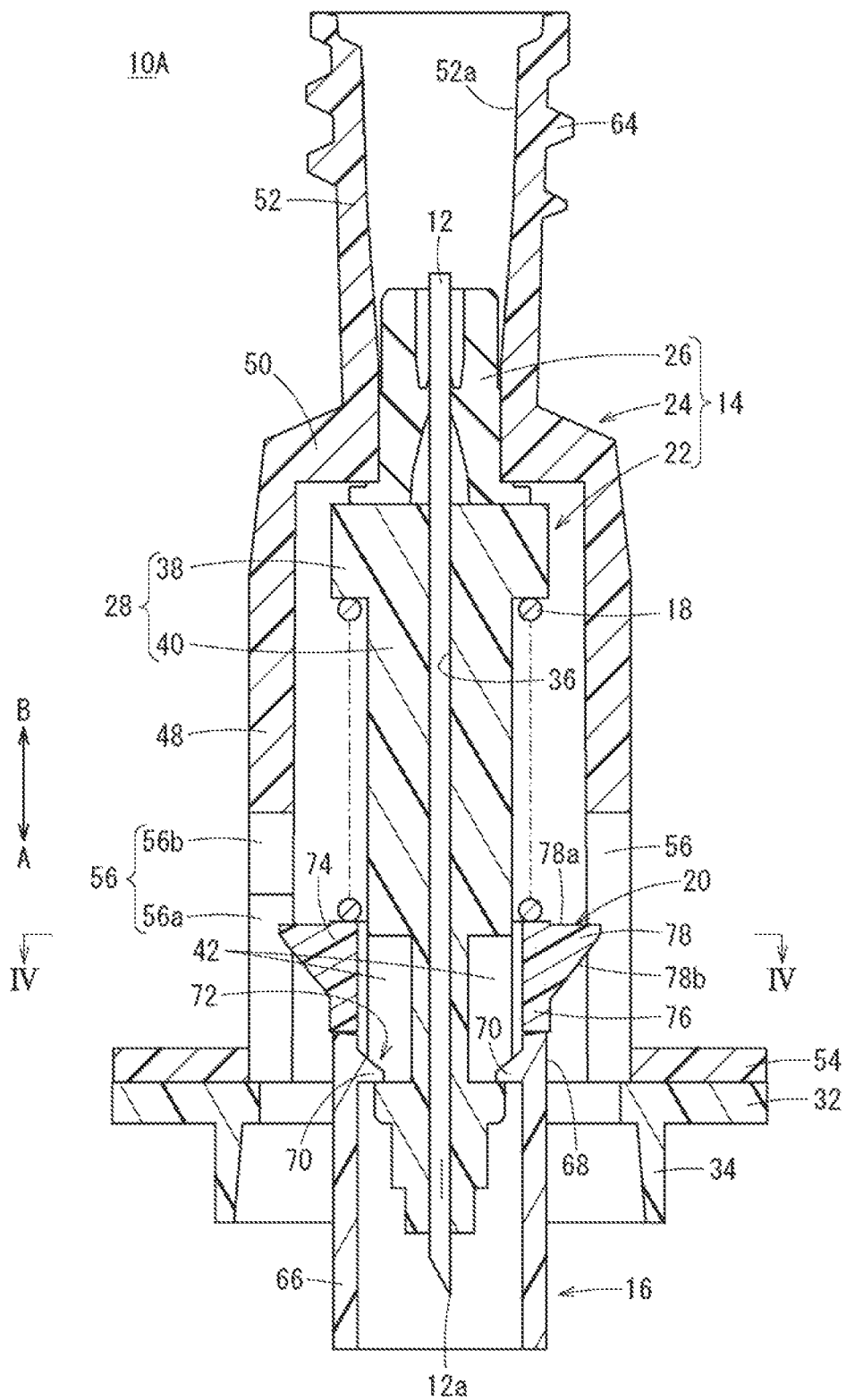
FIG. 2 is a longitudinal sectional view of the needle assembly of FIG. 1.

As shown in FIG. 2, the needle assembly 10A includes a tubular needle 12 having a needle tip 12a. In the following description, in the needle assembly 10A and its components, the direction in which the needle tip 12a of the tubular needle 12 is located (the direction of arrow A in FIG. 2) is referred to as the distal direction, and the opposite direction (the direction of arrow B in FIG. 2) is referred to as the proximal direction.

Figure 1:
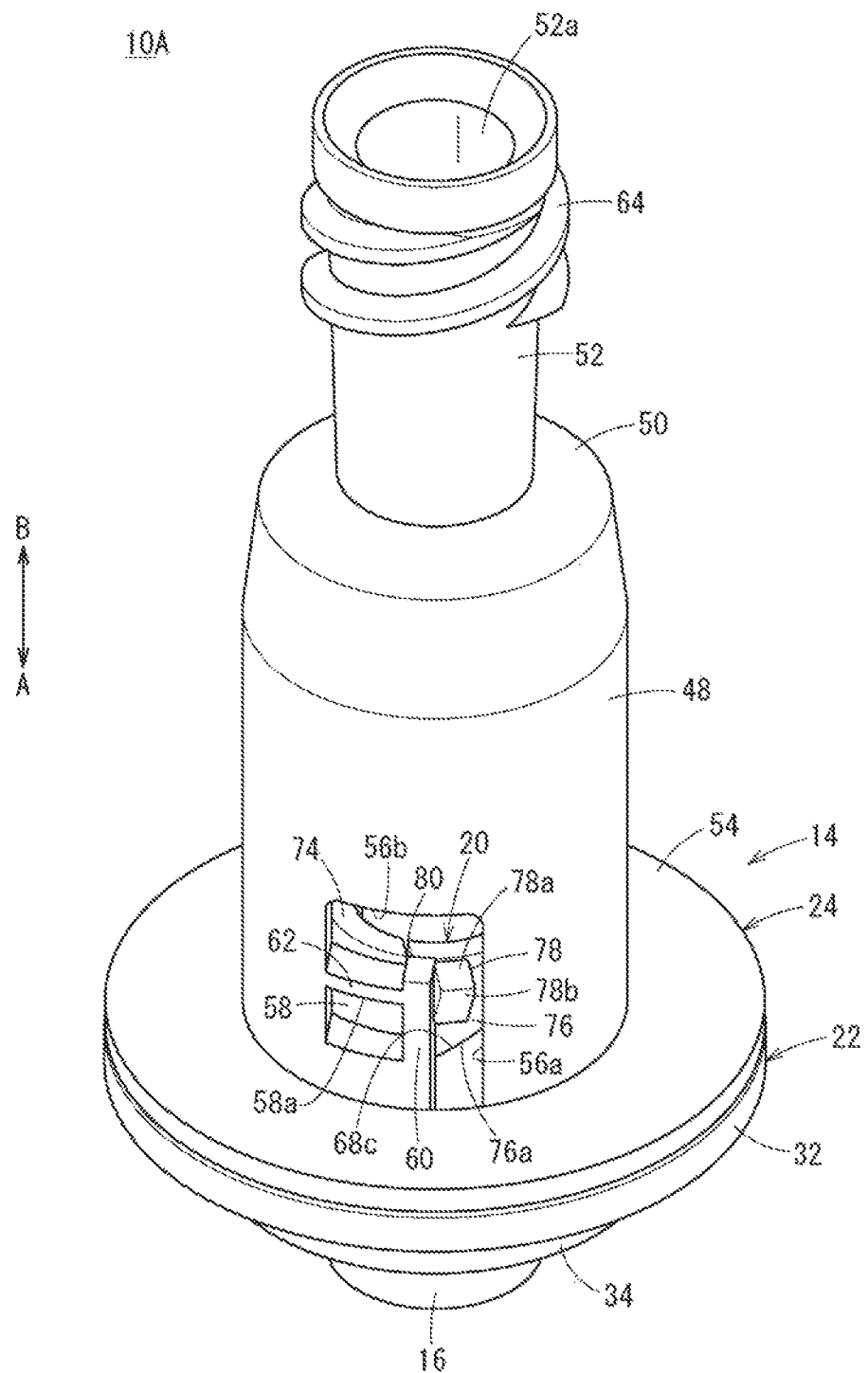
FIG. 1 is a perspective view of a needle assembly according to a first embodiment.
Figure 3:
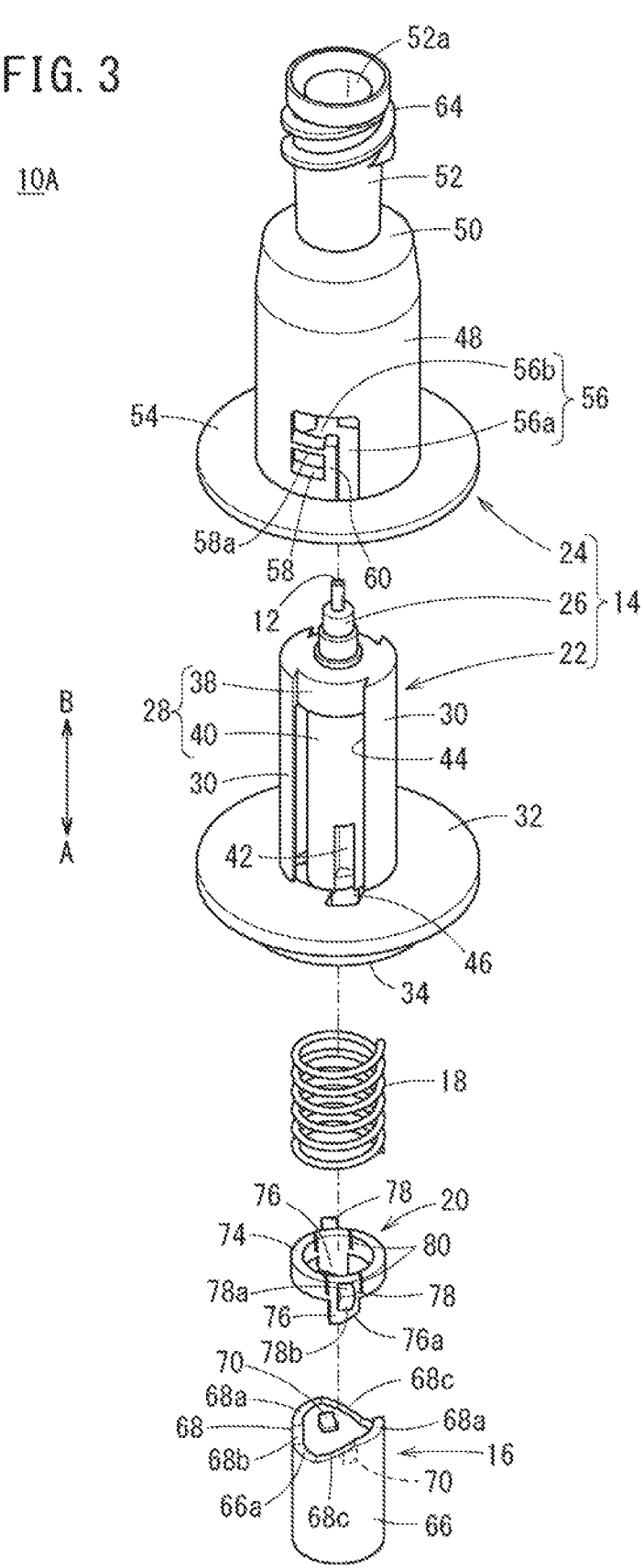
FIG. 3 is an exploded perspective view of the needle assembly of FIG. 1.

As shown in FIGS. 1 to 3, the needle assembly 10A includes the tubular needle 12, a needle hub 14, a needle protection member 16, an urging member 18, and a rotor 20.

Figure 4:
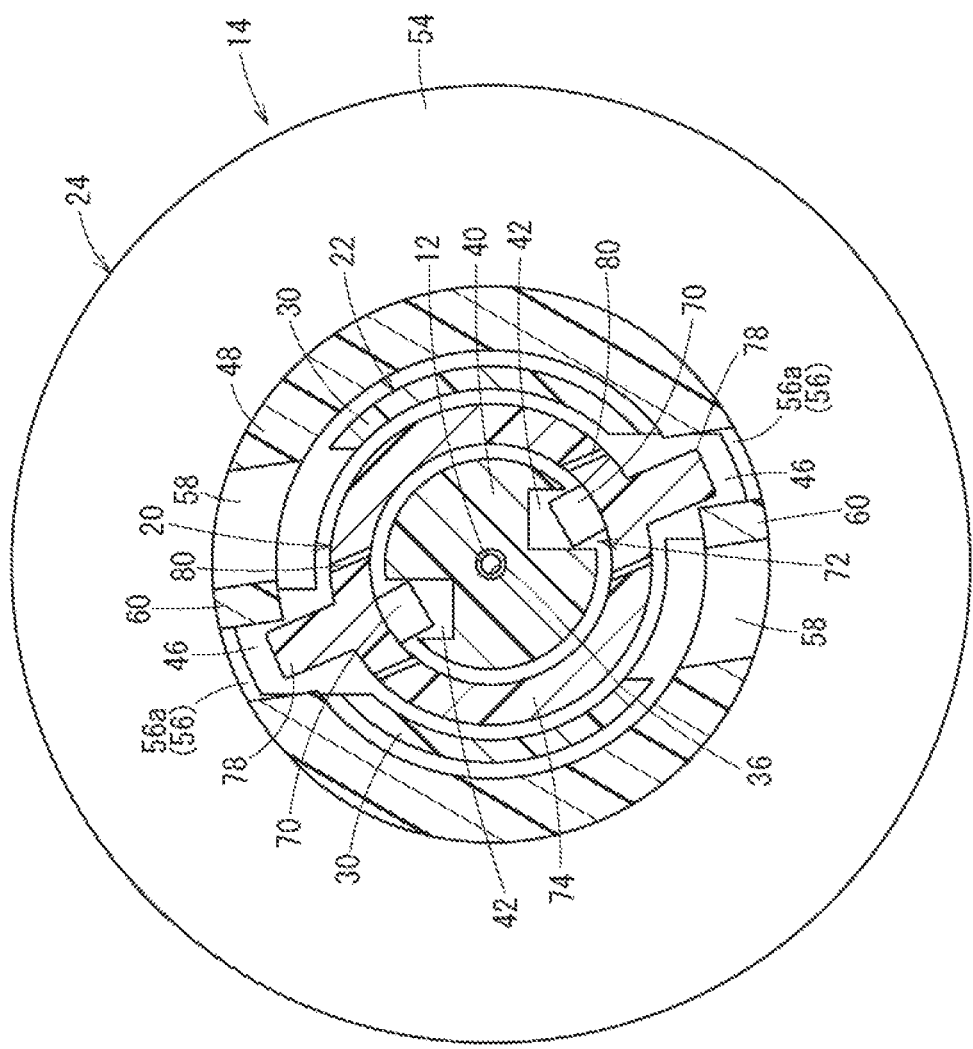
FIG. 4 is a sectional view taken along line IV-IV in FIG. 2.

As shown in FIGS. 2 and 4, the tubular needle 12 is a hollow tubular member and has the sharp needle tip 12a at the tip. Examples of materials from which the tubular needle 12 may be fabricated include a metal material such as stainless steel, aluminum, aluminum alloy, titanium, and titanium alloy, or a hard resin material such as polyphenylene sulfide.

The outer diameter of the tubular needle 12 can be, for example, 0.2 mm to 0.45 mm. The projecting length of the tubular needle 12 from the needle hub 14 (the length of the exposed portion) can be, preferably, for example, 0.5 mm to 1.4 mm in order to reliably inject the drug M intradermally 308.

In FIGS. 2 and 3, the needle hub 14 includes a first hub 22 that holds the tubular needle 12, a second hub 24 provided on the first hub 22, and an elastic member 26 that holds the proximal end of the tubular needle 12. Each of the first hub 22 and the second hub 24 can be made of a synthetic resin such as polycarbonate, polypropylene, and polyethylene.

The first hub 22 includes a needle holding portion 28, a pair of support wall portions 30, a first flange portion 32, and a distal end tubular portion 34. The needle holding portion 28 has an insertion hole 36 through which the tubular needle 12 is inserted. The needle holding portion 28 includes a first end wall portion 38 that includes a proximal end of the first hub 22, and a needle holding body 40 extending in a distal direction from a substantially central portion of the first end wall portion 38. A pair of long grooves 42 extending along the axial direction of the tubular needle 12 can be formed on the outer face of the needle holding body 40.

As shown in FIGS. 3 and 4, the pair of support wall portions 30 extend from the outer peripheral portion of the first end wall portion 38 toward the distal direction of the tubular needle 12 so as to sandwich the needle holding body 40 from radial outside of the tubular needle 12. A gap is formed between the support wall portion 30 and the needle holding body 40. An opening 44 extending in the axial direction of the tubular needle 12 is formed between the pair of support wall portions 30 (see FIG. 3).

In FIGS. 2 and 3, the first flange portion 32 projects radially outward of the tubular needle 12 from the extending end of each support wall portion 30, and extends one circumference in the circumferential direction. In accordance with an embodiment, the first flange portion 32 has two assembling holes 46 communicating with the inner holes. These assembling holes 46 are necessary when assembling the rotor 20 in the gap between the needle holding body 40 and the support wall portion 30.

The distal end tubular portion 34 projects from the face, of the first flange portion 32, that is directed toward the distal direction of the tubular needle 12 toward distal direction. The projecting end face of the distal end tubular portion 34 is located toward the proximal direction of the tubular needle 12 relative to the needle tip 12a and extends in a direction orthogonal to the axial direction of the tubular needle 12 (see FIG. 2).

The second hub 24 includes an outer tubular portion 48 provided so as to cover the pair of support wall portions 30, a second end wall portion 50 provided at a proximal end of the outer tubular portion 48, a connection portion 52 provided on the second end wall portion 50, and a second flange portion 54 provided at the distal end of the outer tubular portion 48. The outer tubular portion 48 is formed in a cylindrical shape. A gap is formed between the second end wall portion 50 and the first end wall portion 38 (see FIG. 2).

Figure 5A:
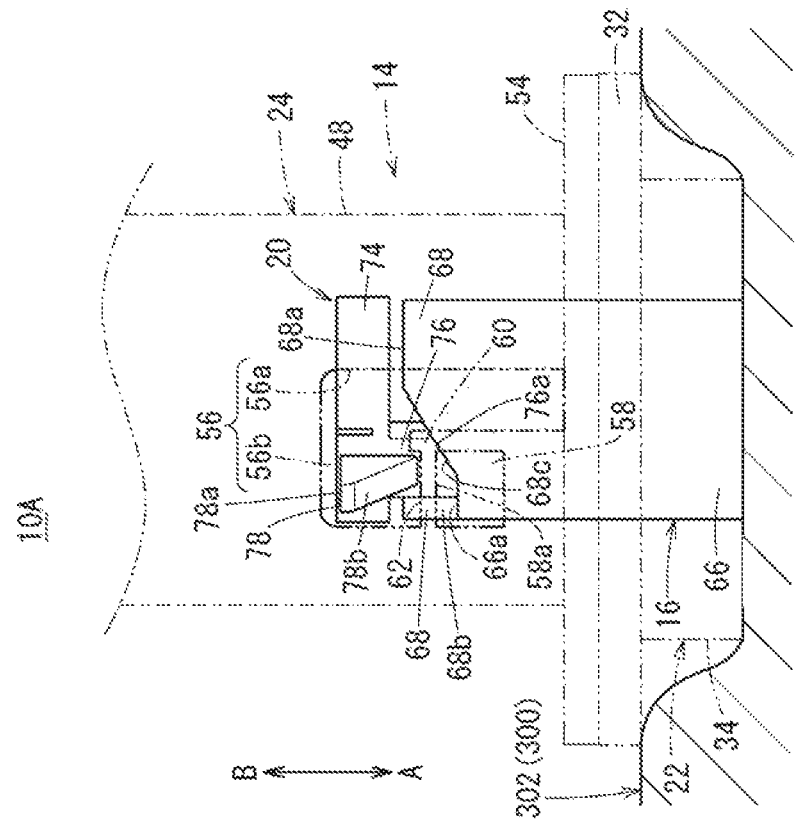
FIG. 5A is a first operation explanatory view of the needle assembly of FIG. 1.

The outer tubular portion 48 is provided around the outer periphery of the rotor 20. As shown in FIGS. 1, 3, and 5A, the outer tubular portion 48 has a pair of recessed guide passages 56 and a pair of recessed lock portions 58. Each of the pair of guide passages 56 and the pair of lock portions 58 is positioned with each phase shifted by 180° (i.e., arranged on opposite sides of the tubular needle 12 at 180° from each other) in the circumferential direction of the tubular needle 12 (see FIG. 4).

The guide passage 56 is a hole that penetrates the outer tubular portion 48 in the radial direction of the tubular needle 12. The guide passage 56 has a first hole 56a extending along the axial direction of the tubular needle 12 from the distal end of the outer tubular portion 48 toward the proximal direction, and a second hole 56b extending in the circumferential direction of the tubular needle 12 from the proximal end of the first hole 56a.

The pair of lock portions 58 is positioned with the phase shifted by 180° (i.e., arranged on opposite sides of the tubular needle 12 at 180° from each other) in the circumferential direction of the tubular needle 12. The lock portion 58 is a square hole located in the circumferential direction of the tubular needle 12 of the first hole 56a and in the proximal direction of the second hole 56b. The lock portion 58 and the first hole 56a are separated from each other by a first wall portion 60 extending along the axial direction of the tubular needle 12.

The lock portion 58 and the second hole 56b are separated from each other by a second wall portion 62 extending along the circumferential direction of the tubular needle 12. The first wall portion 60 and the second wall portion 62 are connected to each other. The proximal end of the first wall portion 60 projects slightly toward the proximal direction relative to the second wall portion 62.

As shown in FIGS. 2, 3, and 6, the connection portion 52 is a tubular portion extending in the proximal direction from substantially the center of the second end wall portion 50, and is configured to be connectable to the connection portion 202 of a prefilled syringe 200. The inner face 52a of the connection portion 52 has an expanding diameter with a taper extending toward the proximal direction, and comes into liquid-tight contact with the outer face 205 of a nozzle portion 204 of the prefilled syringe 200. A male screw portion 64 is provided on the outer face of the connection portion 52. The male screw portion 64 is screwed into a female screw portion 206 of the prefilled syringe 200. Note that the connection portion 202 is formed separately from the nozzle portion 204, and can be attached to the nozzle portion 204.

In FIGS. 2 and 3, the second flange portion 54 projects radially outward of the tubular needle 12 from the distal end of the outer tubular portion 48 and extends one circumference in the circumferential direction (i.e., extends around the distal end of the outer tubular portion 48 for 360 degrees). The face of the second flange portion 54 that is directed toward the distal direction is fixed to the face of the first flange portion 32 that is directed toward the proximal direction by ultrasonic welding or the like. The outer diameter of the second flange portion 54 is substantially the same as the outer diameter of the first flange portion 32.

The elastic member 26 holds the proximal end of the tubular needle 12, and is provided in the second hub 24. The elastic member 26 is fabricated from, for example, a rubber material. The elastic member 26 is in liquid-tight contact with the inner face 52a of the connection portion 52 while being sandwiched between the first end wall portion 38 and the second end wall portion 50.

The needle protection member 16 is a protector (sheath) for protecting the needle tip 12a, and has a generally cylindrical shape. The needle protection member 16 is provided on the needle hub 14 to be displaceable along the axial direction of the tubular needle 12 between a protection position at which the needle tip 12a is covered (the position of the needle protection member 16 shown in FIG. 2) and a use position at which the needle tip 12a is exposed (the position of the needle protection member 16 shown in FIG. 6). Thus, the needle protection member 16 is located at a use position where the needle tip 12a is exposed by being displaced in the proximal direction of the tubular needle 12 from the protection position at which the needle tip 12a is covered.

The tubular needle 12 and the distal end of the needle holding body 40 are inserted through the inner hole of the needle protection member 16. The needle protection member 16 includes a cylindrical portion 66 and a pair of projections 68 projecting in the proximal direction from the proximal end face 66a of the cylindrical portion 66. The pair of projections 68 are arranged on opposite sides of the tubular needle 12 in the circumferential direction of the tubular needle 12. Each of the projections 68 extend along the circumferential direction of the tubular needle 12. The width of the projection 68 along the circumferential direction of the tubular needle 12 decreases in the proximal direction.

Each of the projections 68 has a projecting end face 68a, a first side face 68b, and a second side face 68c. The projecting end face 68a extends in a direction orthogonal to the axial direction of the tubular needle 12. The first side face 68b extends in the distal direction from one end of the projecting end face 68a in the circumferential direction of the tubular needle 12 along the axial direction of the tubular needle 12. The second side face 68c is an inclined surface that is inclined, opposite to the first side face 68b, from the other end of the projecting end face 68a in the circumferential direction of the tubular needle 12 toward the distal direction. That is, the second side face 68c is inclined in the axial direction of the tubular needle 12 toward the circumferential direction of the tubular needle 12.

The first side face 68b and the second side face 68c, of the projection 68, that are adjacent to each other are connected by the proximal end face 66a of the cylindrical portion 66. The proximal end face 66a extends in a direction orthogonal to the axial direction of the tubular needle 12. The projecting end face 68a, the first side face 68b, the second side face 68c, and the proximal end face 66a constitute the proximal end face of the needle protection member 16.

In FIGS. 2 to 4, a support claw 70 is provided on the inner face of each projection 68 (the inner face of the needle protection member 16). The support claw 70 is provided in each of the pair of long grooves 42 of the needle holding body 40. The support claw 70 is in contact with the groove side face of the long groove 42 so that the rotation of the needle protection member 16 with respect to the needle hub 14 in the circumferential direction of the tubular needle 12 is restricted (see FIG. 4). That is, the pair of long grooves 42 and the pair of support claws 70 function as a rotation restriction portion 72 that restricts the rotation of the needle protection member 16 with respect to the needle hub 14 along the circumferential direction of the tubular needle 12.

The rotor 20 is provided at the proximal end of the needle protection member 16. The rotor 20 is integrally formed of a flexible resin material. Examples of materials from which the rotor 20 can be fabricated include the resin materials same as those of the first hub 22 and the second hub 24 described above. The rotor 20 includes an annular rotor body 74, a pair of protrusions 76, and a pair of restriction portions 78. The inner diameter of the rotor body 74 is substantially the same as the inner diameter of the needle protection member 16, and the outer diameter of the rotor body 74 is substantially the same as the outer diameter of the needle protection member 16.

The pair of protrusions 76 are arranged at positions where the phases are shifted by 180° (i.e., arranged on opposite sides of the rotor 20 and 180° from each other) in the circumferential direction of the rotor body 74. The protrusion 76 extend from an end face of the rotor body 74 facing toward the distal direction, and the protrusions 76 extend in the distal direction. A contact face 76a parallel to the second side face 68c of the needle protection member 16 is formed at the projecting end of the protrusion 76. The contact face 76a comes into surface contact with the second side face 68c. The length (i.e., width) of the contact face 76a along the circumferential direction of the tubular needle 12 is shorter than the length (i.e., width) of the second side face 68c along the circumferential direction of the tubular needle 12. The restriction portion (regulating portion) 78 projects radially outward of the tubular needle 12 from the outer faces of the rotor body 74 and the protrusion 76.

The face of the restriction portion 78 that is directed toward the proximal direction can be a restriction face 78a that extends in a direction orthogonal to the axial direction of the tubular needle 12. The face of the restriction portion 78 that is directed radially outward of the tubular needle 12 can be a tapered face 78b that is inclined radially inward of the tubular needle 12 toward the distal direction.

Slits 80 which are opened in the other end face, of the rotor body 74, that is directed toward the proximal direction are formed on both sides of the restriction portion 78 of the rotor body 74. The slit 80 extends from the other end face, of the rotor body 74, that is directed toward the proximal direction toward the distal direction up to a position just before of the protrusion 76. Note that the slit 80 may not be provided.

In FIGS. 1 and 5A, the restriction portion 78 is inserted into the guide passage 56 in an initial state (a state before use) of the needle assembly 10A. In FIGS. 5B to 8A, when the needle protection member 16 in the initial state is displaced from the protection position to the use position and returns to the protection position, the restriction portion 78 is displaced from the initial position (the position of the first hole 56a) to the lock position (the position of the lock portion 58) by the rotation of the rotor body 74 with respect to the needle protection member 16. That is, the guide passage 56 guides the restriction portion 78 at the initial position to the lock position.

The face of the lock portion 58 of the second wall portion 62 functions as a displacement prevention portion 58a that helps prevent the needle protection member 16 from being displaced from the protection position to the use position again by the contact of the restriction portion 78 at the lock position.

As shown in FIGS. 2 and 3, the urging member 18 is provided on the needle hub 14 to urge the rotor 20 and the needle protection member 16 in the distal direction, and for example, the urging member can be a compression coil spring. However, the urging member 18 is not limited to a compression coil spring, but may be various spring members or a rubber member.

The urging member 18 is disposed between the needle hub 14 and the rotor 20. Specifically, one end (the end in the distal direction) of the urging member 18 is in contact with the proximal end face of the rotor body 74. The other end (the end in the proximal direction) of the urging member 18 is in contact with a face of the first end wall portion 38 that is directed toward the distal direction. The needle holding body 40 is inserted through the inner hole of the urging member 18.

Next, the operation of the needle assembly 10A will be described.

First, the user takes out the needle assembly 10A shown in FIG. 1 from a case (not shown). At this time, since the needle protection member 16 is at the protection position at which the needle tip 12a is covered, the user does not touch the needle tip 12a. Further, the restriction portion 78 of the rotor 20 is located in the first hole 56a.

Then, the connection portion 202 of the prefilled syringe 200 filled with the drug M is connected to the connection portion 52 of the needle hub 14 (see FIG. 6). In particular, the male screw portion 64 of the needle hub 14 is screwed into the female screw portion 206 of the prefilled syringe 200, and the outer face 205 of the nozzle portion 204 of the prefilled syringe 200 is brought into liquid-tight contact with the inner face 52a of the connection portion 52 of the needle hub 14. At this time, the distal end face of the nozzle portion 204 is in liquid-tight contact with the elastic member 26.

Thereafter, as shown in FIG. 5A, the distal end face of the needle protection member 16 is pressed against the epidermis 304 of the skin 302. Then, a reaction force acts on the needle protection member 16 in the proximal direction (the direction of the arrow B). Therefore, the needle protection member 16 at the protection position moves in the proximal direction against the urging force of the urging member 18. At this time, the needle protection member 16 does not rotate in the circumferential direction of the tubular needle 12 with respect to the needle hub 14 due to the action of the rotation restriction portion 72 (see FIG. 4).

Figure 5B:
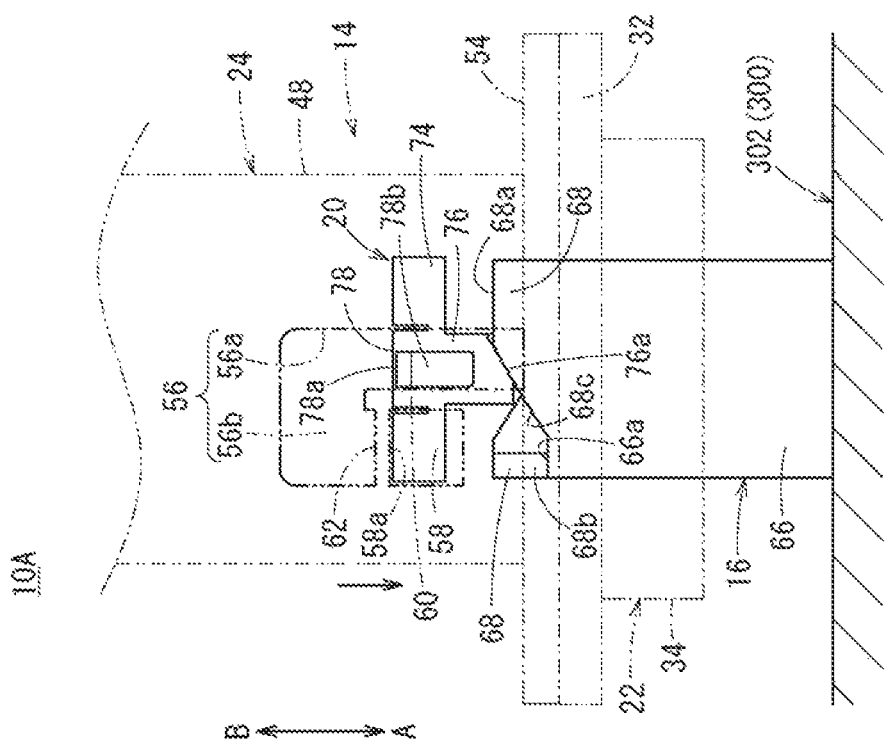
FIG. 5B is a second operation explanatory view of the needle assembly of FIG. 1.

At this time, as shown in FIGS. 5A and 5B, the projection 68 of the needle protection member 16 presses the protrusion 76 of the rotor 20 in the proximal direction. Therefore, the restriction portion 78 displaces the first hole 56a in the proximal direction while the rotation is restricted by the first wall portion 60. When the restriction portion 78 is displaced toward the proximal direction relative to the first wall portion 60, the rotor 20 rotates in the circumferential direction of the tubular needle 12 while the contact face 76a of the rotor 20 slides on the second side face 68c toward the proximal end face 66a with further displacement of the needle protection member 16 toward the proximal direction.

That is, the restriction portion 78 is displaced in the circumferential direction of the tubular needle 12 along the second hole 56b. As a result, the restriction portion 78 is located in the proximal direction of the second wall portion 62, and the needle protection member 16 is displaced in the proximal direction from the protection position to the use position where the needle tip 12a is exposed (see FIG. 6). At this time, the contact face 76a of the rotor 20 is away (i.e., not in contact) from the second side face 68c of the needle protection member 16, and the projecting end face of the rotor 20 contacts the proximal end face 66a of the cylindrical portion 66.

Also, due to the displacement of the needle protection member 16 in the proximal direction, the needle tip 12a exposed toward the distal end of the needle protection member 16 punctures the epidermis 304, and the needle tip 12a is located intradermally 308 (in the dermis) by pressing the needle assembly 10A against the epidermis 304 until the first flange portion 32 contacts the epidermis 304. The user presses a pusher (not shown) of the prefilled syringe 200 to inject the drug M in the prefilled syringe 200 intradermally 308 via the tubular needle 12.

Thereafter, the needle hub 14 is separated from the epidermis 304, whereby the tubular needle 12 is withdrawn intradermally 308. Then, as shown in FIG. 7A, the rotor 20 is pushed in the distal direction by the urging force of the urging member 18 in a state where the tapered face 78b of the restriction portion 78 is in contact with the second wall portion 62. As a result, since the restriction portion 78 is pushed radially inward of the tubular needle 12 by the second wall portion 62, the portion of the rotor body 74 where the restriction portion 78 is provided (the portion between the two slits 80) is elastically deformed radially inward of the tubular needle 12.

Therefore, as shown in FIGS. 7B and 8A, the restriction portion 78 extends over in a distal direction the second wall portion 62 (displacement prevention portion 58a) to be located in the lock portion 58. Further, the needle protection member 16 at the use position is pushed by the urging member 18 in the distal direction (the direction of the arrow A) and returns to the protection position. At this time, for the needle protection member 16, the support claw 70 of the needle protection member 16 comes into contact with the wall face (the surface located in the distal direction) constituting the long groove 42.

Therefore, as shown in FIG. 8B, for example, even when the user accidentally presses the needle protection member 16 in the proximal direction, the needle protection member 16 is prevented from moving from the protection position to the use position again by the restriction face 78a of the restriction portion 78 coming into contact with the second wall portion 62. That is, the safety function for preventing the needle tip 12a from being exposed from the needle protection member 16 is activated.

That is, the needle assembly 10A has a construction in which after the needle protection member 16 is displaced for the first time from the protection position to the use position, a second time displacement of the needle protection member 16 from the protection position to the use position is prevented by the contact between the restriction portion 78 and the second wall portion 62.

Next, effects of the needle assembly 10A according to the present embodiment will be described below.

In the needle assembly 10A, when the needle protection member 16 in the initial state is displaced from the protection position to the use position and returns to the protection position, the restriction portion 78 of the rotor 20 is displaced from the initial position to the lock position by the rotation of the rotor body 74 with respect to the needle protection member 16. The needle hub 14 includes the displacement prevention portion 58a that helps prevent the needle protection member 16 from being re-displaced from the protection position to the use position by contacting the restriction portion 78 at the lock position.

As a result, the safety function can be reliably activated. Further, since the needle protection member 16 is not rotated in the circumferential direction of the tubular needle 12, the discomfort given to the drug recipient 300 due to the skin 302 being pulled in the rotation direction when the needle protection member 16 is displaced from the protection position to the use position can be suppressed.

The needle assembly 10A includes the rotation restriction portion 72 that restricts the rotation of the needle protection member 16 with respect to the needle hub 14 along the circumferential direction of the tubular needle 12. As a result, when the needle protection member 16 is displaced from the protection position to the use position, the rotation of the needle protection member 16 with respect to the skin 302 can be effectively suppressed.

The second side face 68c (inclined surface) that is inclined in the axial direction of the tubular needle 12 toward the circumferential direction of the tubular needle 12 is provided on the proximal end face of the needle protection member 16. The rotor 20 has the protrusion 76 that projects from the rotor body 74 toward the distal direction of the tubular needle 12 and contacts the inclined surface. As a result, the rotor 20 can be rotated in the circumferential direction of the tubular needle 12 with respect to the needle protection member 16 with a rather simple configuration.

The protrusion 76 has the contact face 76a that comes into surface contact with the second side face 68c. As a result, it is possible to prevent an excessive pressure from acting on the protrusion 76 from the needle protection member 16.

In accordance with an embodiment, two sets of second side faces 68c and protrusions 76 are provided in the circumferential direction of the tubular needle 12. As a result, excessive pressure can be prevented from acting on the protrusion 76 from the needle protection member 16.

The restriction portion 78 projects from the protrusion 76 radially outward of the tubular needle 12. As a result, the rigidity of the protrusion 76 can be improved by the restriction portion 78.

The outer tubular portion 48 of the needle hub 14 is provided with the recessed guide passage 56 for guiding the restriction portion 78 at the initial position to the lock position. As a result, the restriction portion 78 at the initial position can be reliably guided to the lock position.

The outer tubular portion 48 is provided with the guide passage 56, the recessed lock portion 58 that is located in the distal direction of the tubular needle 12 relative to the guide passage 56 and that composes the displacement prevention portion 58a. When the needle protection member 16 returns from the use position to the protection position by the urging force of the urging member 18, the restriction portion 78 in the guide passage 56 gets (i.e., extends) over the second wall portion 62 (displacement prevention portion 58a) in the distal direction and is inserted into the lock portion 58. As a result, the needle hub 14 and the rotor 20 can have a rather simple configuration.

The slits 80 which are opened in the face, of the rotor body 74, that is directed toward the proximal direction are formed on both sides of the restriction portion 78 of the rotor body 74. The rotor body 74 is elastically deformed radially inward of the tubular needle 12 when the restriction portion 78 gets (i.e., extends) over the displacement prevention portion 58a. As a result, the restriction portion 78 can rather easily get (extend) over the displacement prevention portion 58a.

The guide passage 56 and the lock portion 58 are not limited to the through holes, but may be grooves formed on the inner face of the outer tubular portion 48. One set (i.e., a pair or two) of the guide passage 56 and the lock portion 58 may be provided, or three or more of the guide passages 56 and the lock portions 58 may be provided. The displacement prevention portion 58a may be a projection that projects radially inward of the tubular needle 12 from the inner face of the outer tubular portion 48.

The projection 68 of the needle protection member 16 and the corresponding protrusion 76 of the rotor 20, and the guide passage 56 of the outer tubular portion 48 of the second hub 24 and the corresponding restriction portion 78 of the rotor 20 may not be a pair for each, but corresponding components may be provided one by one.

Second Embodiment

Next, a needle assembly 10B according to the second embodiment of the present disclosure will be described. In the needle assembly 10B according to the second embodiment, the components same as those of the needle assembly 10A described in the first embodiment are denoted by the same reference numerals, and the detailed description of the components as those of the needle assembly 10A described in the first embodiment is omitted. In the needle assembly 10B according to the second embodiment, for the same configuration as the needle assembly 10A, the same effects as the effects described in the first embodiment can be obtained.

Figure 9:
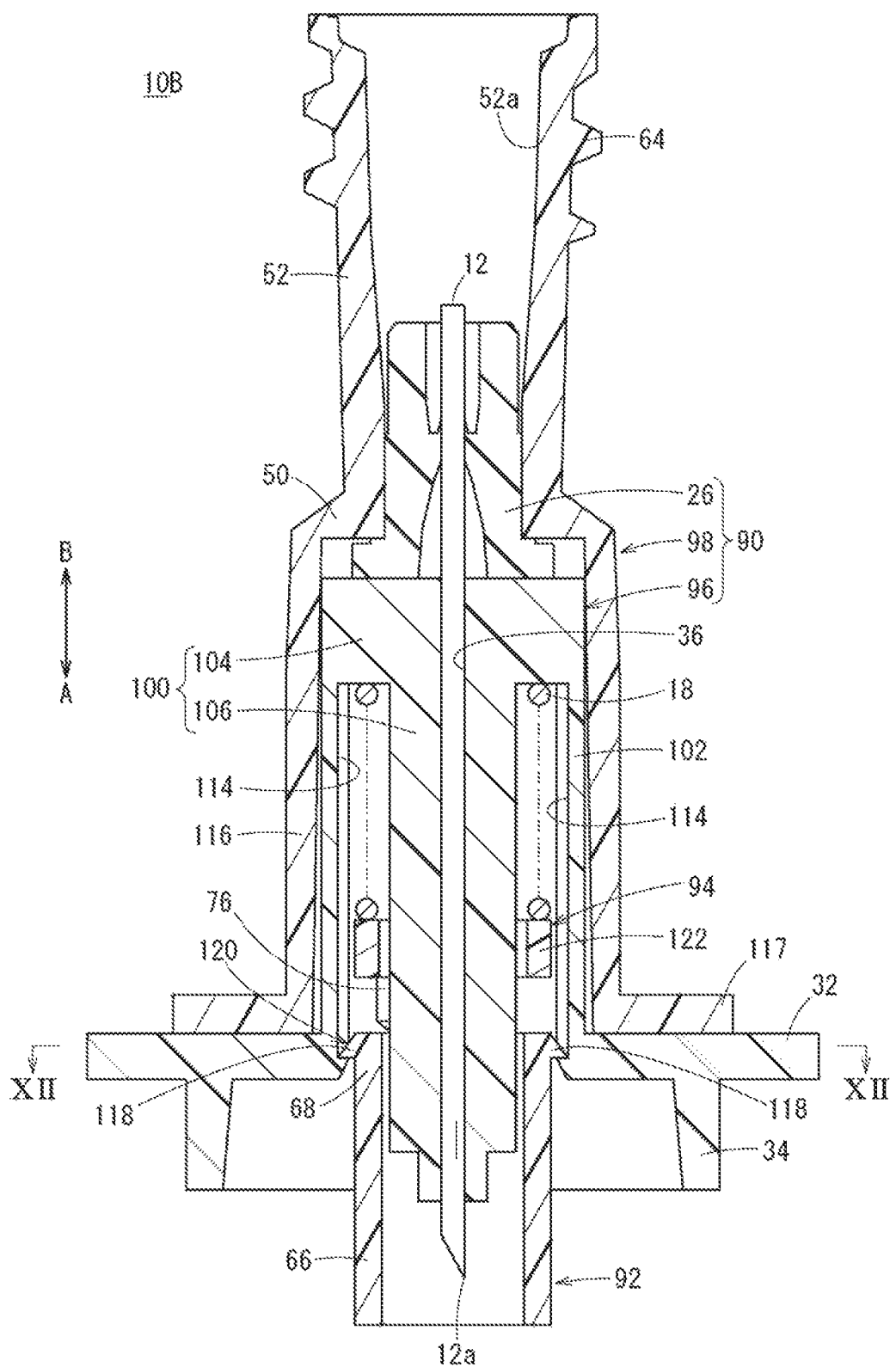
FIG. 9 is a longitudinal sectional view of a needle assembly according to a second embodiment.
Figure 10:
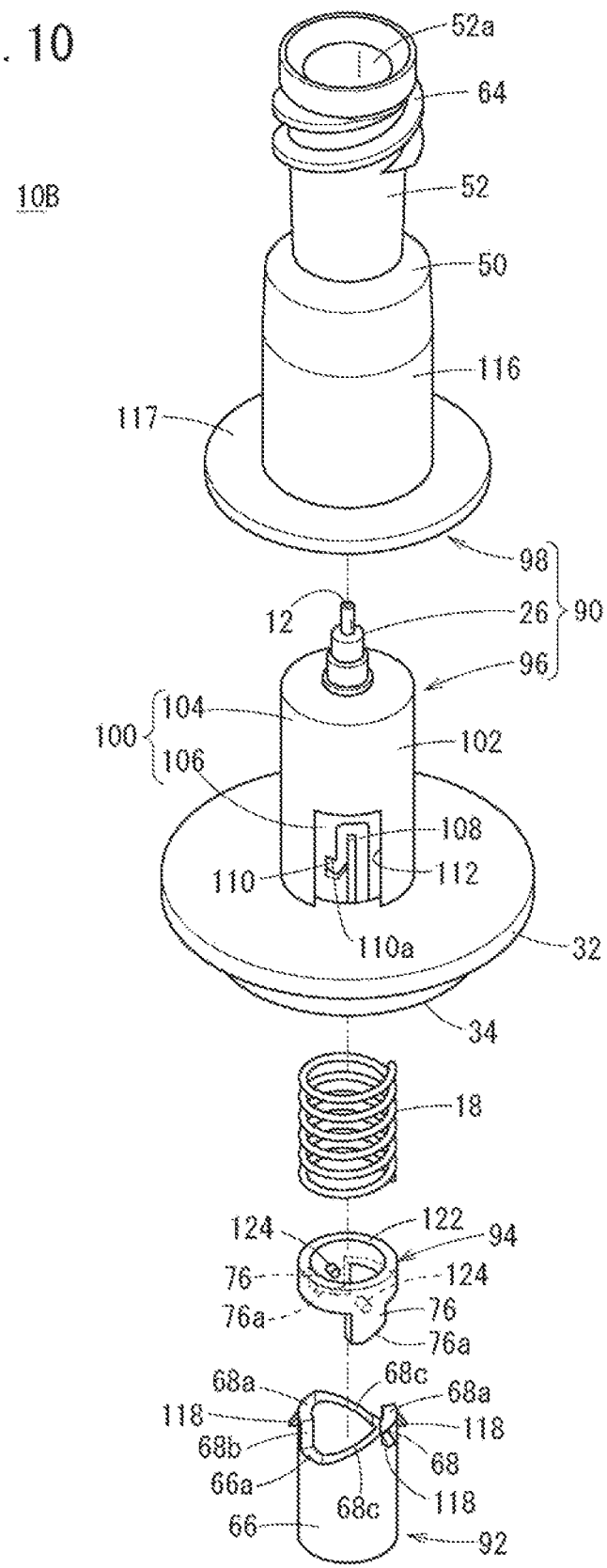
FIG. 10 is an exploded perspective view of the needle assembly of FIG. 9.

As shown in FIGS. 9 and 10, the needle assembly 10B includes the tubular needle 12, a needle hub 90, a needle protection member 92, the urging member 18, and a rotor 94. The needle hub 90 includes a first hub 96 that holds the tubular needle 12, a second hub 98 provided on the first hub 96, and the elastic member 26 that holds the proximal end of the tubular needle 12.

Figure 11:
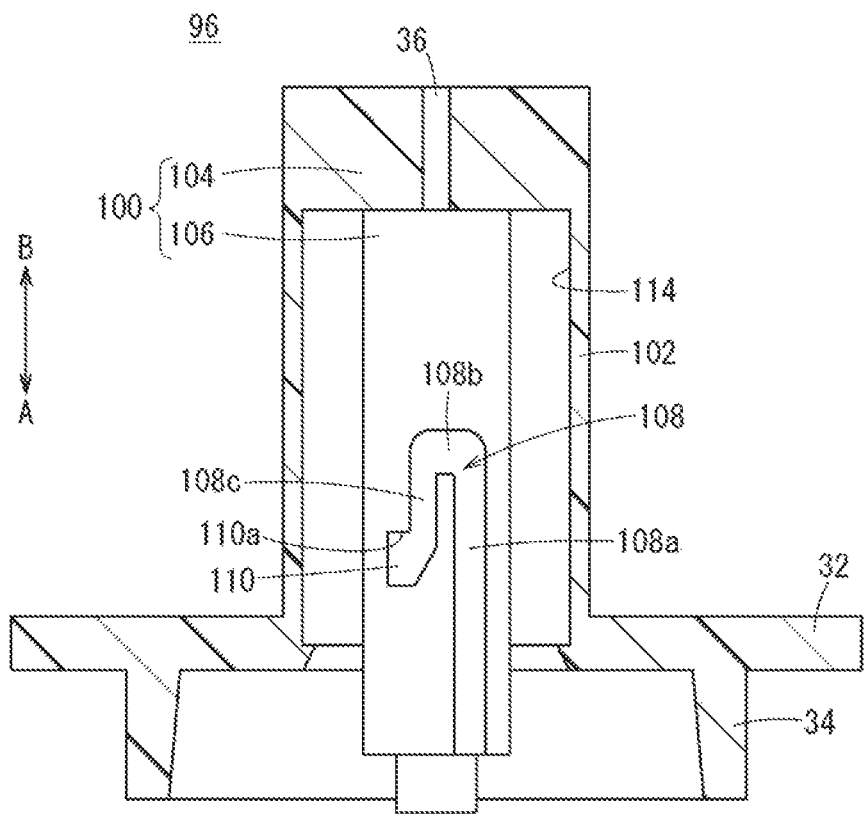
FIG. 11 is a partial cross-sectional plan view of a first hub of FIG. 9.

In FIG. 11, the first hub 96 has a needle holding portion 100, an inner tubular portion 102, the first flange portion 32, and the distal end tubular portion 34. The needle holding portion 100 has the insertion hole 36 through which the tubular needle 12 is inserted. The needle holding portion 100 includes a first end wall portion 104 that composes a proximal end of the first hub 96, and a needle holding body 106 extending in a distal direction from a substantially central portion of the first end wall portion 104. A pair of recessed guide passages 108 and a pair of recessed lock portions 110 are formed on the outer face of the needle holding portion 100. Each of the pair of guide passages 108 and the pair of lock portions 110 is positioned with each phase shifted by 180° (i.e., arranged on opposite sides of the tubular needle 12 at 180° from each other) in the circumferential direction of the tubular needle 12.

The guide passage 108 is a groove formed on the outer face of the needle holding body 106. The guide passage 108 has a first groove 108a, a second groove 108b, and a third groove 108c. The first groove 108a extends along the axial direction of the tubular needle 12 from the distal end of the needle holding body 106 toward the proximal end. The second groove 108b extends in the circumferential direction of the tubular needle 12 from the proximal end of the first groove 108a. The third groove 108c extends in the distal direction from the end, of the second groove 108b, that is opposite to the first groove 108a. The lock portion 110 extends in the circumferential direction of the tubular needle 12 (in the direction away from the first groove 108a) from the end of the third groove 108c in the distal direction.

In FIG. 10, the inner tubular portion 102 has a pair of openings 112. Each of the openings 112 is a rectangular hole, and is formed in the inner tubular portion 102 at a position facing the guide passage 108 and the lock portion 110. That is, the pair of openings 112 is positioned with the phase shifted by 180° (i.e., arranged on opposite sides of the tubular needle 12 at 180° from each other) in the circumferential direction of the tubular needle 12.

Figure 12:
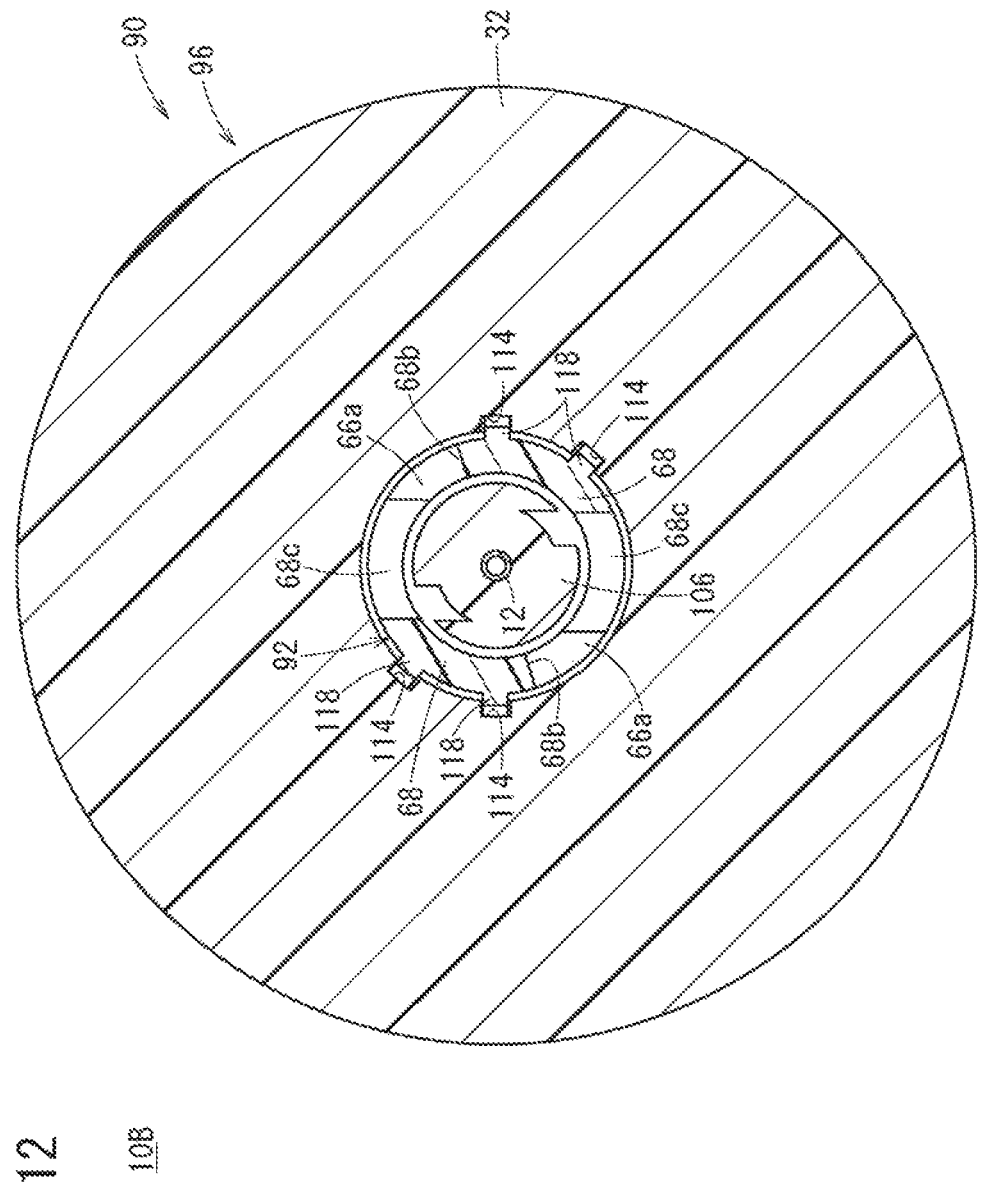
FIG. 12 is a sectional view taken along line XII-XII in FIG. 9.

As shown in FIGS. 9, 11, and 12, four long grooves 114 are formed on the inner face of the inner tubular portion 102. The long groove 114 extends from the proximal end of the inner tubular portion 102 to slightly before one end (the end in the distal direction) of the inner face constituting the inner hole of the first flange portion 32.

In FIGS. 9 and 10, the second hub 98 has an outer tubular portion 116, the second end wall portion 50, the connection portion 52, and a second flange portion 117. The outer tubular portion 116 differs from the outer tubular portion 48 only in that the guide passage 56 and the lock portion 58 of the first embodiment are not formed. The outer diameter of the second flange portion 117 is smaller than the outer diameter of the first flange portion 32.

The needle protection member 92 has the cylindrical portion 66 and the projection 68. Two support claws 118 provided in the long groove 114 are provided on the outer face of each projection 68. The support claw 118 is in contact with the groove side face the long groove 114 so that the rotation of the needle protection member 92 with respect to the needle hub 90 in the circumferential direction of the tubular needle 12 is restricted (see FIG. 12). That is, the four long grooves 114 and the four support claws 118 function as a rotation restriction portion 120 that restricts the rotation of the needle protection member 92 with respect to the needle hub 90 along the circumferential direction of the tubular needle 12.

As shown in FIG. 10, the rotor 94 has a rotor body 122, a pair of protrusions 76, and a pair of restriction portions 124. The rotor body 122 differs from the rotor body 74 described above only in that the slit 80 of the first embodiment is not formed. The restriction portion 124 protrudes radially inward of the tubular needle 12 from the inner faces of the rotor body 122 and the protrusion 76. The restriction portion 124 is formed in a columnar shape.

Figure 13A:
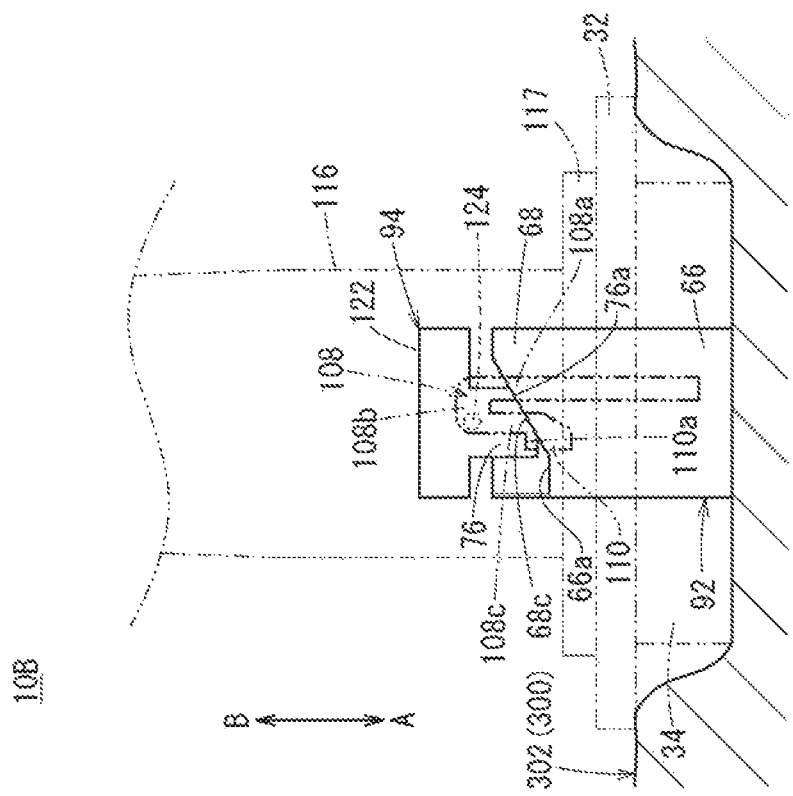
FIG. 13A is a first operation explanatory view of the needle assembly of FIG. 9.

In FIG. 13A, the restriction portion 124 is inserted into the guide passage 108 in an initial state (a state before use) of the needle assembly 10B. In FIGS. 13B to 15A, when the needle protection member 92 in the initial state is displaced from the protection position to the use position and returns to the protection position, the restriction portion 124 is displaced from the initial position (the position of the first groove 108a) to the lock position (the position of the lock portion 110) by the rotation of the rotor body 122 with respect to the needle protection member 92. That is, the guide passage 108 guides the restriction portion 124 at the initial position to the lock position.

A portion located in the proximal direction (a portion that is directed toward the distal direction) of the face of the lock portion 110 functions as a displacement prevention portion 110a that helps prevent the needle protection member 92 from being displaced from the protection position to the use position again by contact of the restriction portion 124 at the lock position.

Next, the operation of the needle assembly 10B will be described.

As shown in FIG. 13A, the restriction portion 124 of the rotor 94 in the initial state is located in the first groove 108a in the initial state of the needle assembly 10B. Then, the connection portion 202 of the prefilled syringe 200 filled with the drug M is connected to the connection portion 52 of the needle hub 90 (see FIG. 14). Thereafter, the distal end face of the needle protection member 92 is pressed against the epidermis 304 of the skin 302.

As a result, a reaction force in the proximal direction (the direction of arrow B) acts on the needle protection member 92. Therefore, the needle protection member 92 at the protection position moves in the proximal direction against the urging force of the urging member 18. At this time, the needle protection member 92 does not rotate in the circumferential direction of the tubular needle 12 with respect to the needle hub 90 due to the action of the rotation restriction portion 120.

Figure 13B:
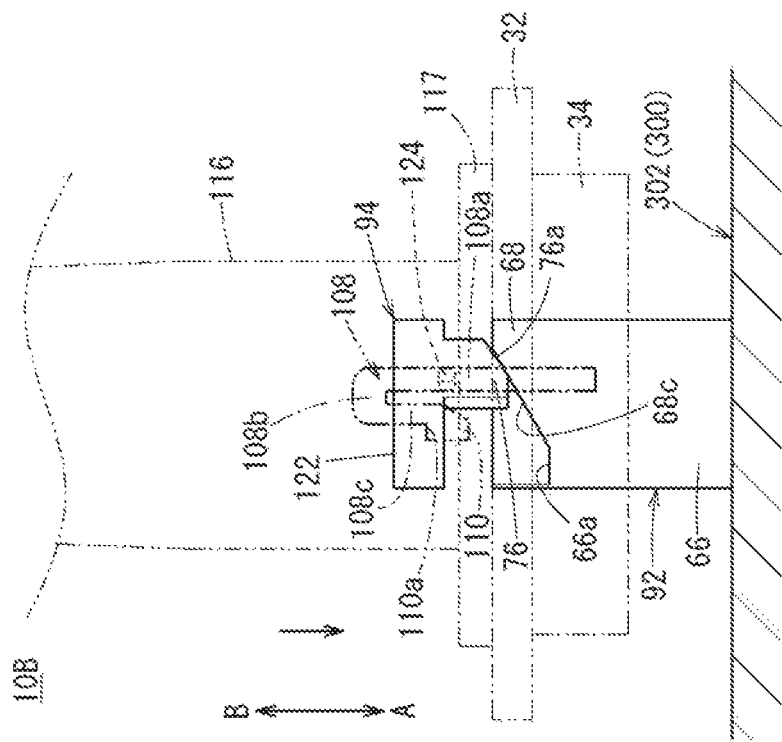
FIG. 13B is a second operation explanatory view of the needle assembly of FIG. 9.
Figure 14:
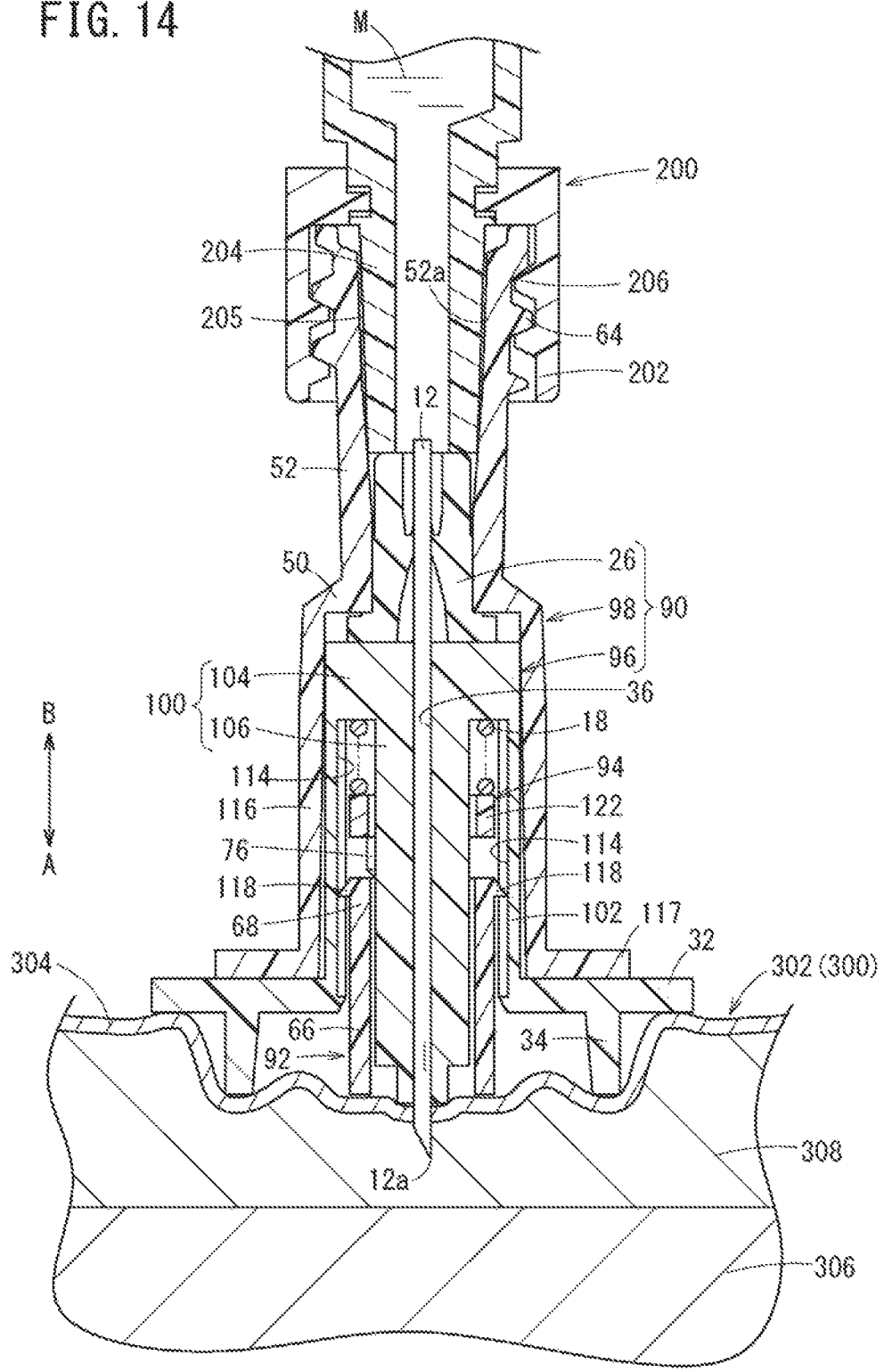
FIG. 14 is an explanatory sectional view showing a state where a drug is injected intradermally by the needle assembly of FIG. 9.

At this time, as shown in FIGS. 13A and 13B, the projection 68 of the needle protection member 92 presses the protrusion 76 of the rotor 94 in the proximal direction. Therefore, the restriction portion 124 is displaced in the first groove 108a in the proximal direction in a state where the rotation is restricted by the groove side face of the first groove 108a. When the restriction portion 124 is displaced to the proximal end of the first groove 108a, the rotor 94 rotates in the circumferential direction of the tubular needle 12 while the contact face 76a of the rotor 94 slides on the second side face 68c toward the proximal end face 66a with displacement of the needle protection member 92 toward the proximal direction.

That is, the restriction portion 124 moves in the circumferential direction of the tubular needle 12 along the second groove 108b. As a result, the restriction portion 124 is located in the proximal direction of the third groove 108c, and the needle protection member 92 is displaced in the proximal direction from the protection position to the use position where the needle tip 12a is exposed (see FIG. 14).

Also, due to the displacement of the needle protection member 92 in the proximal direction, the needle tip 12a exposed toward the distal end of the needle protection member 92 punctures the epidermis 304, and the needle tip 12a is located intradermally 308 (in the dermis) by pressing the needle assembly 10B against the epidermis 304 until the first flange portion 32 contacts the epidermis 304. The user presses a pusher (not shown) of the prefilled syringe 200 to inject the drug M in the prefilled syringe 200 intradermally 308 via the tubular needle 12.

Thereafter, the needle hub 90 is separated from the epidermis 304, whereby the tubular needle 12 is withdrawn intradermally 308. Then, the rotor 94 is pushed in the distal direction by the urging force of the urging member 18. As a result, the restriction portion 124 moves in the distal direction in the third groove 108c in a state where the rotation is restricted by the groove side face of the third groove 108c.

When the restriction portion 124 moves to the distal end of the third groove 108c, the rotor 94 rotates in the circumferential direction of the tubular needle 12 while the contact face 76a of the rotor 94 slides on the second side face 68c toward the proximal end face 66a. As a result, as shown in FIG. 15A, the restriction portion 124 is located inside the lock portion 110. Further, the needle protection member 92 at the use position is pushed by the urging member 18 in the distal direction (the direction of the arrow A) and returns to the protection position. At this time, for the needle protection member 92, the support claw 118 of the needle protection member 92 comes into contact with the wall face (the surface located in the distal direction) of the long groove 114.

Therefore, as shown in FIG. 15B, even when the user accidentally presses the needle protection member 92 in the proximal direction, the needle protection member 92 is prevented from moving from the protection position to the use position again by the restriction portion 124 coming into contact with the lock portion 110. That is, the safety function for preventing the needle tip 12a from being exposed from the needle protection member 92 is activated.

That is, the needle assembly 10B has a construction in which after the needle protection member 92 is displaced for the first time from the protection position to the use position, a second time displacement of the needle protection member 92 from the protection position to the use position is prevented by the contact between the restriction portion 124 and the displacement prevention portion 110a.

In the needle assembly 10B, the restriction portion 124 projects radially inward of the tubular needle 12 from the protrusion 76, and the needle hub 90 has the inner tubular portion 102 which is disposed radially inward of the tubular needle 12 relative to the rotor 94 and has a guide passage 108. As a result, the needle hub 90 and the rotor 94 can be made compact.

One set (i.e., a pair or two) of the guide passages 108 and the lock portions 110 may be provided, or three or more of the guide passages 108 and the lock portions 110 may be provided. The displacement prevention portion 110a may be a protrusion that protrudes radially outward of the tubular needle 12 from the outer face of the needle holding body 106.

The projection 68 of the needle protection member 92 and the corresponding protrusion 76 of the rotor 94, and the guide passage 108 of the needle holding portion 100 and the corresponding restriction portion 124 of the rotor 94 may not be a pair for each, but corresponding components may be provided one by one.

The needle assembly according to the present disclosure is not limited to the above-described embodiment, but, of course, may have various configurations without departing from the gist of the present disclosure. For example, the syringe may not be a prefilled syringe, but may be a syringe filled with a drug solution (i.e., medical solution) immediately before use.

The detailed description above describes embodiments of a needle assembly for injecting a drug intradermally. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims

What is claimed is:

1. A needle assembly for injecting a drug intradermally, the needle assembly comprising;
   a tubular needle that includes a needle tip;
   a needle hub supporting the tubular needle, the needle hub including a first hub configured to hold the tubular needle, a second hub provided on the first hub, and an elastic member configured to hold a proximal end of the tubular needle;
   a needle protection member displaceable along an axial direction of the tubular needle;
   a rotor provided at a proximal end of the needle protection member, the rotor includes a rotor body and a restriction portion, the restriction portion being provided on the rotor body and projects radially outward of the tubular needle, and the needle hub having an outer tubular portion of the second hub disposed around an outer periphery of the rotor, and wherein the restriction portion is displaced from an initial position to a lock position by the rotor body rotating with respect to the needle protection member; and
   wherein the needle hub includes a displacement prevention portion configured to prevent the needle protection member from being re-displaced by contacting the restriction portion at the lock position, the displacement prevention portion being a projection that projects radially inward from an inner face of the needle protection member; and
   a rotation restriction portion configured to restrict a rotation of the needle protection member with respect to the needle hub along a circumferential direction of the tubular needle, the rotation restriction portion formed from the projection that projects radially inward from the inner face of the needle protection member and an elongated groove in the first hub of the needle hub.

2. The needle assembly according to claim 1, wherein
   a proximal end face of the needle protection member has an inclined surface that is inclined in an axial direction of the tubular needle toward a circumferential direction of the tubular needle, and wherein the rotor has a protrusion that projects from the rotor body toward the distal direction of the tubular needle and contacts the inclined surface; and
   the protrusion including a contact face that comes into surface contact with the inclined surface.

3. The needle assembly according to claim 2, comprising:
a plurality of the inclined surfaces and a plurality of the protrusions provided in the circumferential direction of the tubular needle.

4. The needle assembly according to claim 2, wherein the restriction portion projects from the protrusion along a radial direction of the tubular needle.

5. The needle assembly according to claim 4, wherein the needle hub has a recessed guide passage for guiding the restriction portion at the initial position to the lock position.

6. The needle assembly according to claim 5, wherein the restriction portion projects radially outward of the tubular needle from the protrusion, the outer tubular portion including the guide passage, and a recessed lock portion that is located in a distal direction of the tubular needle relative to the guide passage and composes the displacement prevention portion.

7. The needle assembly according to claim 5, wherein the recessed guide passage comprises a pair of recessed guide passages and a pair of recessed lock portions in the outer tubular portion of the second hub, each of the pair of guide passages and the pair of lock portions is positioned with each phase shifted by 180 degrees in the circumferential direction of the tubular needle.

8. The needle assembly according to claim 7, wherein the pair of guide passages are through holes that penetrate the outer tubular portion of the second hub in a radial direction of the tubular needle.

9. The needle assembly according to claim 7, wherein the pair of guide passages each have has a first hole extending along the axial direction of the tubular needle from a distal end of the outer tubular portion toward a proximal direction of the needle assembly, and a second hole extending in the circumferential direction of the tubular needle from a proximal end of the first hole; and
   each of the pair of lock portions is a hole located in the circumferential direction of the tubular needle of the first hole and in the proximal direction of the second hole, wherein each of the pair of lock portions and the first hole is separated from each other by a first wall portion extending along the axial direction of the tubular needle.

10. A needle assembly for injecting a drug intradermally, the needle assembly comprising:
    a tubular needle that includes a needle tip;
    a needle hub supporting the tubular needle, the needle hub including a first hub configured to hold the tubular needle, a second hub provided on the first hub, and an elastic member configured to hold a proximal end of the tubular needle;
    a needle protection member displaceable along an axial direction of the tubular needle;
    a rotor provided at a proximal end of the needle protection member;
    an urging member provided on the needle hub configured to urge the rotor and the needle protection member toward a distal direction of the tubular needle;
    the needle protection member is located at a use position at which the needle tip is exposed when displaced in a proximal direction of the tubular needle from a protection position at which the needle tip is covered;
    the rotor includes a rotor body and a restriction portion, the restriction portion being provided on the rotor body and projects radially outward of the tubular needle, and the tubular needle having an outer tubular portion of the second hub disposed around an outer periphery of the rotor, and wherein the restriction portion is displaced from an initial position to a lock position by the rotor body rotating with respect to the needle protection member when the needle protection member in an initial state is displaced from the protection position to the use position and returns to the protection position; and
    wherein the needle hub is provided with a displacement prevention portion configured to prevent the needle protection member from being re-displaced from the protection position to the use position by contacting the restriction portion at the lock position, the displacement prevention portion being a projection that projects radially inward from an inner face of the needle protection member; and
    a rotation restriction portion configured to restrict a rotation of the needle protection member with respect to the needle hub along a circumferential direction of the tubular needle, the rotation restriction portion formed from the projection that projects radially inward from the inner face of the needle protection member and an elongated groove in the first hub of the needle hub.

11. The needle assembly according to claim 10, wherein a proximal end face of the needle protection member has an inclined surface that is inclined in an axial direction of the tubular needle toward a circumferential direction of the tubular needle, and wherein the rotor has a protrusion that projects from the rotor body toward the distal direction of the tubular needle and contacts the inclined surface.

12. The needle assembly according to claim 11, wherein the protrusion has a contact face that comes into surface contact with the inclined surface.

13. The needle assembly according to claim 11, comprising:
    a plurality of the inclined surfaces and a plurality of the protrusions provided in the circumferential direction of the tubular needle.

14. The needle assembly according to claim 11, wherein the restriction portion projects from the protrusion along a radial direction of the tubular needle.

15. The needle assembly according to claim 14, wherein the needle hub has a recessed guide passage for guiding the restriction portion at the initial position to the lock position.

16. The needle assembly according to claim 15, wherein the restriction portion projects radially outward of the tubular needle from the protrusion, the outer tubular portion including the guide passage, and a recessed lock portion that is located in a distal direction of the tubular needle relative to the guide passage and composes the displacement prevention portion; and
    wherein when the needle protection member returns from the use position to the protection position by an urging force of the urging member, the restriction portion in the guide passage gets over the displacement prevention portion in the distal direction of the tubular needle to be inserted into the lock portion.

17. The needle assembly according to claim 16, comprising:
    slits which are open in a face of the rotor body are formed on both sides of the restriction portion of the rotor body, the face being directed toward the proximal direction of the tubular needle; and
    wherein the rotor body is elastically deformed radially inward of the tubular needle when the restriction portion gets over the displacement prevention portion.

18. The needle assembly according to claim 16, wherein the restriction portion has a tapered face that is inclined radially inward of the tubular needle toward the distal direction of the tubular needle.

19. The needle assembly according to claim 15, wherein the restriction portion projects radially inward of the tubular needle, and the needle hub has a needle holding body disposed radially closer to the tubular needle than the rotor body.

20. The needle assembly according to claim 10, wherein the urging member is a spring or a rubber member.

* * * * *